(12) United States Patent
Hudgins et al.

(10) Patent No.: US 7,919,542 B2
(45) Date of Patent: Apr. 5, 2011

(54) PHASE SEPARATED, BRANCHED, COPOLYMER HYDROGEL

(75) Inventors: Robert Garryl Hudgins, Monticello, MN (US); Jim M. Criss, Jr., Marietta, GA (US)

(73) Assignee: Zimmer Spine, Inc., Minneapolis, MN (US)

( * ) Notice: Subject to any disclaimer, the term of this patent is extended or adjusted under 35 U.S.C. 154(b) by 439 days.

(21) Appl. No.: 11/938,488

(22) Filed: Nov. 12, 2007

(65) Prior Publication Data

US 2009/0124722 A1 May 14, 2009

(51) Int. Cl.
*A61F 2/02* (2006.01)
*C08F 8/34* (2006.01)

(52) U.S. Cl. ......... 523/115; 524/916; 525/374; 528/492
(58) Field of Classification Search .................. 523/115; 524/916; 525/374; 528/492
See application file for complete search history.

(56) References Cited

U.S. PATENT DOCUMENTS

| | | | |
|---|---|---|---|
| 5,147,344 A * | 9/1992 | Sachau et al. ................. | 604/368 |
| RE34,296 E * | 6/1993 | Roesink et al. ................ | 521/50 |
| 5,240,862 A * | 8/1993 | Koenhen et al. .............. | 436/178 |
| 6,387,978 B2 * | 5/2002 | Ronan et al. .................... | 523/113 |
| 7,214,245 B1 | 5/2007 | Marcolongo et al. | |
| 2004/0033242 A1* | 2/2004 | McDonald et al. ............ | 424/400 |
| 2005/0154199 A1* | 7/2005 | Whiteford et al. ............ | 540/145 |
| 2006/0100304 A1 | 5/2006 | Vresilovic et al. | |
| 2006/0188487 A1 | 8/2006 | Thomas et al. | |

OTHER PUBLICATIONS

S. Andre et al., New Fluorinated Themoplastic Elastomers. III. Novel Method of Synthesis and Characterization of Alternating Fluorinated Polyimide/Fluorinated Polyhybridsiloxane Block Copolymers via Polycondensation; Journal of Polymer Science, Part A: Polymer Chemistry, vol. 43, 2237-2247 (2005).

Liu et al., Synthesis, Structure, and Properties of Polyimide and Polyurethane-urea-imide Copolymers; Journal of Polymer Science: Part B: Polymer Physics, vol. 42, 216-225 (2004).

Mallakpour et al., Synthesis and Characterization of new Optically Active Ply(amide-Imide-Urethane) Thermoplastic Elastomers, Dericed from 4,4'-(Hexafluoroisopropylidene)-N, N'-bis(phthaloyl-L-leucine-p-aminobenzoic Acid) and PEG-MDI; Journal of Applied Polymer Science, vol. 91, 2288-2294 (2004).

Banu et al., Thermoplastic Poly(ester-imide)s Derived from Anhydride-Terminated Polyester Prepolymer and Diisocyanate; Journal of Polymer Science: Part A: Polymer Chemistry, vol. 42, 341-350 (2004).

S. Andre et al., New Fluorinated Thmoplastic Elastomers. II. Synthesis and Characterization of Perfectly Alternating Fluorinated Polyimide-Fluorinated Polyhybridsiloxane Block Copolymers via Polyhydrosilylation; Journal of Polymer Science, Part A: Polymer Chemistry, vol. 42, 200-207 (2004).

Zuo et al., Preparation and Characterization of Poly(urethane-imide) Films prepared from Reactive Polyimide and Polyurethane Prepolymer; Polymer, vol. 40, 5153-5160 (1999).

* cited by examiner

*Primary Examiner* — Tae H Yoon
(74) *Attorney, Agent, or Firm* — Seager, Tufte & Wickhem, LLC (57) ABSTRACT

The present invention provides a hydrogel composition comprising a mixture of a hydrophilic polymer and a polymer chain modifying agent, wherein the polymer chain modifying agent is selected from the group consisting of an aromatic tetracarboxylic dianhydride, a titanate, and a polyetherimide. The present invention also provides a method for producing a phase separated, branched, copolymer hydrogel comprising a mixture of a hydrophilic polymer and a polymer chain modifying agent. The present invention also provides an implantable medical device comprising a phase separated, branched, copolymer hydrogel wherein the phase separated, branched, copolymer hydrogel is formed of a hydrophilic polymer and a polymer chain modifying agent.

7 Claims, 5 Drawing Sheets

PHASE SEPARATED, BRANCHED, COPOLYMER HYDROGEL

TECHNICAL FIELD

This invention relates to a hydrogel material, and specifically, a phase separated, branched, copolymer hydrogel that is suitable for biomedical or other applications.

BACKGROUND

Hydrogels are water-swellable or water-swollen materials typically having a structure defined by a crosslinked network of hydrophilic homopolymers or copolymers. The hydrophilic homopolymers or copolymers may be water-soluble in free form, but in a hydrogel, they are rendered insoluble (but swellable) in water due to covalent, ionic, or physical crosslinking. In the case of physical crosslinking, the linkages may take the form of entanglements, crystallites, or hydrogen-bonded structures. The crosslinks in a hydrogel provide structure and physical integrity to the network.

Hydrogels may be classified as amorphous, semicrystalline, hydrogen-bonded structures, supermolecular structures, or hydrocolloidal aggregates. Numerous parameters affect the physical properties of a hydrogel, including molecular weight of gel polymer, type of crosslinking, and crosslinking density. The crosslinking density, for example, influences the hydrogels macroscopic properties, such as storage modulus (E'), which is a measure of the energy stored during a cycle of elongation or compression. Pore size and shape, pore density, and other factors can also impact the surface properties, optical properties, and mechanical properties of a hydrogel.

Hydrogels have been derived from a variety of hydrophilic polymers and copolymers. Polyvinyl alcohol (PVA), polyethylene glycol (PEG), polyvinyl pyrrolidone (PVP), polyacrylamide (PA), polyhydroxyethyl methacrylate (PHEMA), and copolymers of the foregoing, are examples of polymers from which hydrogels have been made. Hydrogels have also been formed from biopolymers such as chitosan, agarose, hyaluronic acid and gelatin, as well as interpenetrating network (IPN) hydrogels such as gelatin crosslinked with poly(ethylene glycol) diacrylate.

Hydrogels have shown promise in biomedical and pharmaceutical applications, mainly due to their high water content and rubbery or pliable nature, which can mimic natural tissue and can facilitate the release of bioactive substances at a desired physiological site. For example, hydrogels have been used and/or proposed in a variety of tissue treatment applications, including as implants, tissue adhesives, bone grafts for spinal and orthopedic treatments such as meniscus and articular cartilage replacement, and intervertebral disc nucleoplasty. One drawback to the use of conventional hydrogels in certain tissue treatment applications, and in particular bone tissue treatments, is that such hydrogels are typically weak materials that fracture easily and do not have desired levels of durability and wear resistance. Devices made from PVA hydrogels have been observed to fail due to wear, such as by tearing, abrasion, or shredding.

In the context of nucleoplasty, where the nucleus pulposum of the intervertebral disc is replaced with a prosthetic, simple hydrophilic polymeric hydrogels are inadequate. These hydrogels do not possess the required compression strength or toughness needed in the intervertebral disc environment. Polyurethanes do possess the requisite toughness but are difficult to work with because they resist deformation.

Therefore, it would be beneficial to provide hydrogels and methods of making such hydrogels that are similar to polyurethanes in that they are significantly stronger, more durable, and possess improved wear characteristics compared to current hydrogels such as PA, PVA, PVP, and PVA/PVP blends, but that also possess certain characteristics of a hydrogel, namely pliability and high water absorption.

Polyurethane elastomers derive their properties from phase separation into hard (urethane) and soft (polyether or polyester) domains. For instance, spandex, which DuPont sells under the trade name LYCRA®, has both urea and urethane linkages in its backbone. What gives spandex its special properties is the fact that it has hard and soft blocks in its repeat structure. The short polymeric chain of a polyglycol, usually about forty or so repeat units long, is soft and rubbery. The rest of the repeat unit, including the urethane linkages, the urea linkages, and the aromatic groups, is extremely rigid. Thus, polyurethane consists of alternative soft and hard segments, which can self-assemble into two phases. "Phase" is traditionally defined as a homogeneous part of a heterogeneous system. Respectively, "phase separation" is the transformation of a homogeneous system to heterogeneous one.

One way of increasing the mechanical properties of a hydrogel may be to formulate a solid state, phase separated hydrogel. By analogy to polyurethane, a phase separated, branched, copolymer hydrogel may yield improved mechanical properties. However, the absorbent nature of hydrogels that is desirable for biomedical applications needs to be maintained.

Thus, there is a need for a hydrogel having increased mechanical properties that also maintains water absorbent properties and this need can be met with a solid state, phase separated, branched, copolymer hydrogel.

SUMMARY OF THE INVENTION

In one embodiment, the present invention provides a composition comprising a mixture of a hydrophilic polymer and a polymer chain modifying agent. The polymer chain modifying agent is selected from the group consisting of an aromatic tetracarboxylic dianhydride, a titanate, and a polyetherimide. The hydrophilic polymer and polymer chain modifying agent are chemically bonded to one another and form a phase separated, branched, copolymer hydrogel.

In another embodiment, the present invention provides a method for producing a phase separated, branched, copolymer hydrogel. The method comprises mixing a hydrophilic polymer with a polymer chain modifying agent in a mutually compatible solvent and curing the mixture of the hydrophilic polymer and polymer chain modifying agent at an elevated temperature. The polymer chain modifying agent is selected from the group consisting of an aromatic tetracarboxylic dianhydride, a titanate, and a polyetherimide. The present method results in the formation of chemical bonds between the hydrophilic polymer and the polymer chain modifying agent and the production of a phase separated, branched, copolymer hydrogel.

In another embodiment, the present invention provides an implantable medical device comprising a phase separated, branched, copolymer hydrogel. The phase separated, branched, copolymer hydrogel comprises a hydrophilic polymer and a polymer chain modifying agent, wherein the polymer chain modifying agent is selected from the group consisting of an aromatic tetracarboxylic dianhydride, a titanate, and a polyetherimide.

DETAILED DESCRIPTION

The present invention provides phase separated, branched, copolymer hydrogels. Phase separation, as used in herein, means the transformation of a homogenous system in two (or more) phases, as the term is commonly understood in many branches of science and technology (as opposed to separation between solid and liquid, which is correctly defined as separation of states of matter). The phase separated, branched, copolymer hydrogels comprise a mixture of a hydrophilic polymer and a polymer chain modifying agent. The polymer chain modifying agent is selected from the group consisting of an aromatic tetracarboxylic dianhydride, a titanate, and a polyetherimide. The hydrophilic polymer and polymer chain modifying agent are chemically bonded to one another and form a phase separated, branched, copolymer hydrogel. The phase separated, branched, copolymer hydrogel of the invention provides for increased indices of mechanical strength while retaining water adsorption.

In various embodiments, the polymer chain modifying agents provide rigid segments to the resultant polymer and function by at least one of a polymer chain extension agent, a polymer chain branching agent, or a crosslinker. A polymer chain extension agent reacts with at least one of the ends of the polymer chain backbone. A polymer chain branching agent reacts with the polymer chain at a point intermediate the polymer chain ends. In some embodiments, the polymer chain modifying agent forms a pendant group on the hydrophilic polymer. A crosslinking agent reacts with at least two points, the points being either in the same polymer chain or between two polymer chains. Crosslinking within a polymer chain is referred to as an intramolecular crosslink while crosslinking between polymer chains is referred to as an intermolecular crosslink. In various embodiments, the crosslinks formed by the polymer chain modifying agent includes both intramolecular and intermolecular crosslinks.

Aromatic tetracarboxylic dianhydrides include 3,3',4,4'-benzophenone-tetracarboxylic dianhydride, 3,3',4,4'-benzophenonetetracarboxylic dianhydride, 3,3',4,4'-diphenylsulfonetetracarboxylic dianhydride, 3,4,9,10-perylenetetracarboxylic dianhydride, 4,4'-(hexafluoroisopropylidene)diphthalic anhydride, 4,4'-biphthalic anhydride, 4,4'-oxydiphthalic anhydride, naphthalene-1,4,5,8-tetracarboxylic dianhydride, and pyromellitic dianhydride. In one embodiment, the aromatic tetracarboxylic dianhydride is 4,4'-(hexafluoroisopropylidene) diphthalic anhydride (HDA).

Titanates possess a core generally referred to by the formula $TiO_4$ and include alkoxy titanates. In one embodiment, the titanate is titanium (IV) isopropoxide (referred to as TIP), also known as tetraisopropyl titanate.

Polyetherimide (PEI) is an amorphous, high performance thermoplastic with characteristics similar to polyetheretherketone (PEEK). An example of a suitable PEI is ULTEM® (GE Plastics, Pittsfield, Mass.).

Hydrophilic polymers attract and retain water and thus, are primarily responsible for the high water content exhibited by hydrogels. Additionally, the hydrophilic polymer provides the flexible or "soft" segments of the resultant polymer. In one embodiment, the hydrophilic polymer is a polyhydroxy-containing polymer. Specific examples of polyhydroxy, hydrophilic polymers include polyvinyl alcohol, polyacrylamide, polyvinyl pyrrolidone, or polyacrylamide nitrile, or combinations thereof. In one embodiment, the hydrophilic polymer is a mixture, combination, or blend of hydrophilic polymers.

In one embodiment, the hydrophilic polymer is polyvinyl alcohol (PVA) and the polymer chain modifying agent is HDA and forms a PVA/HDA phase separated, branched, copolymer hydrogel. In another embodiment, the hydrophilic polymer is PVA and the polymer chain modifying agent is TIP and forms a PVA/TIP phase separated, branched, copolymer hydrogel. In another embodiment, the hydrophilic polymer is PVA and the polymer chain modifying agent is PEI and forms a PVA/PEI phase separated, branched, copolymer hydrogel.

The present invention also provides a method for producing a phase separated, branched, copolymer hydrogel. According to certain embodiments, the phase separated, branched, copolymer hydrogel is formed by mixing a hydrophilic polymer with a polymer chain modifying agent in a mutually compatible solvent. The polymer chain modifying agent is selected from the group consisting of an aromatic tetracarboxylic dianhydride, a titanate, and a polyetherimide. The mixture of the hydrophilic polymer and polymer chain modifying agent is cured at an elevated temperature. The inventive method results in the formation of chemical bonds between the hydrophilic polymer and the polymer chain modifying agent and the production of a phase separated, branched, copolymer hydrogel.

The present invention also provides an implantable medical device comprising a phase separated, branched, copolymer hydrogel comprising a hydrophilic polymer and a polymer chain modifying agent. The polymer chain modifying agent is selected from the group consisting of an aromatic tetracarboxylic dianhydride, a titanate, and a polyetherimide. In embodiments of the invention, the device of the present invention may be used in biomedical applications and may be suitable for cartilage and intervertebral disc prostheses. For example, a device made from the inventive composition may be used in nucleoplasty and resurfacing of the medial compartment of the tibial plateau.

Without being held to a single theory, the inventive compositions exhibit increased solid-state phase separation due to the formation of a branched polymeric structure. In some embodiments, the portions of the polymeric chain derived from the polymer chain modifying agent form hard segments while the hydrophilic polymer portions form soft segments. In some embodiments, and analogous to polyurethane, the hard and soft segments of the inventive composition segregate into phases. In this context, phase separation refers to the morphology of the solid polymer. Phase separation of the solid state means that the solid polymer exhibits separation of several solids at the micro-structural level.

Optionally, a radiation sensitive material such as a photoinitiator may be added to the phase separated, branched, copolymer hydrogel to facilitate crosslinking of the hydrogel. For example, IRGACURE® photoinitiators (Ciba Specialty Chemicals) may be used to facilitate crosslinking of the inventive composition. Other optional additives include biocompatible preservatives, surfactants, colorants and/or other additives conventionally added to polymer mixtures.

The resultant inventive composition exhibits increased mechanical properties. As a measure of increased mechanical properties, the melting temperature (Tm) and storage capacity of the hydrogel can be ascertained. An increase in Tm relates to an increase in biostability and inertness of the material. The storage capacity of the hydrogel, denoted storage modulus, reflects the extent and amount of water molecules that can be retained within the hydrogel.

The following examples illustrate the synthesis of a hydrophilic polymer to be used as a baseline material for comparison with the inventive compositions comprising a hydrophilic polymer and a polymer chain modifying agent and forming a phase separated, branched, copolymer hydrogel in accordance with certain embodiments of the invention. The resulting hydrogels were subjected to dynamic thermal mechanical analysis (DMTA), including determining the melt temperature and storage modulus.

Example 1

Synthesis of PVA Hydrogel

Polyvinyl alcohol (PVA) was used in two different molecular weight versions, a low molecular weight (LMW) of 31,000-50,000 g/mole and a high molecular weight (HMW) of 130,000 g/mole. The PVA was dried in a vacuum oven at room temperature for 24 hours and stored in a desiccator prior to use.

Solutions of the high and low molecular weight PVA, referred to as HMW PVA and LMW PVA, respectively, and dimethyl sulfoxide (DMSO) were made. A 10 percent by weight (wt. %) solution was made for the LMW. A 7 wt. % solution was used for the HMW PVA due to its increased viscosity over the LMW PVA. Films of 40 mm thickness were cast from these solutions on soda lime glass plates and dried in an oven at 70° C. for 24 hours. The films were then removed and placed in a desiccator. It is noted that thinner films were initially attempted, but were very difficult to remove. It is believed that the hydroxyl groups on the PVA hydrogen bond with the hydroxyl groups on the glass, making thin films hard to remove, such that thicker films were used to obtain high quality films after removal.

Example 2

Synthesis of PVA/HDA Hydrogel 4,4'-(hexafluoroisopropylidene) diphthalic anhydride (HDA) was obtained from Sigma-Aldrich (St. Louis Mo.). Solutions of 10 wt. % and 7 wt. % were made from LMW and HMW PVA, respectively, and DMSO. The HDA was dissolved in DMSO prior to mixing with the PVA solutions. The extent of reaction at gelation, which is the point at which the composition changes from a liquid to a solid, was predicted for both LMW and HMW PVA as a function of moles of HDA.

From this analysis, it was determined to use the mid-point for gelation to assure crosslinking while allowing enough time to cast the films. Therefore, in the reaction, the ratio of 0.5 moles of HDA to 1 mole of HMW PVA was used. The HDA was dissolved in DMSO and added to the HMW PVA while under stirring and at 70° C. This mixture gelled almost instantaneously, so the amount of HDA was reduced to 0.25 moles for the LMW PVA, and the HDA was added to the stirred LMW PVA at room temperature. This mixture did not gel after heating to 110° C. for 1 hr. Films were cast from both materials and put in an oven at 70° C. overnight. Both the HMW PVA/HDA and LMW PVA/HDA films appeared to be more plastic (less waxy) than the PVA films.

The experiment was repeated with HMW and LMW PVA at room temperature using 0.5 moles of HDA. Again, the HMW PVA/HDA mixture gelled almost instantaneously and the LMW PVA did not. Therefore, the reaction was again repeated for the LMW PVA with 3 moles of HDA, which gelled very quickly. Films were cast from these solutions and the mixtures where allowed to cure at 70° C. over night. The resultant films were placed in a desiccator for storage.

Example 3

Synthesis of PVA/TIP Hydrogel

Titanium (IV) isopropoxide (referred to as TIP) was first dissolved in DMSO and then added to the room temperature solutions of 7 wt. % HMW PVA and 10 wt. % LMW PVA and DMSO. High and low TIP concentrations were investigated in an attempt to get both branched and cross-linked structures. Table 1 gives the reaction data and shows that both cross-linked and branched structures appear to have been formed based on whether the solution gelled or not, respectively (i.e., branched only will not gel, cross-linked and branched will gel). The high TIP mole ratios resulted in the solutions gelling, as noticed visually. The lower mole ratios of TIP did not result in a gelled solution prior to casting films. Films were cast from the mixtures and placed in an oven at 70° C. to cure and dry over night. The resultant films were placed in a desiccator.

TABLE 1

PVA/TIP Reaction Data

| REACTION | MW | MOLE PVA | MOLE TIP | TIP/PVA MOLE RATIO | RESULTS |
|---|---|---|---|---|---|
| 1 | HMW | 6.67E−06 | 1.34E−04 | 20 | Gel |
| 2 | LMW | 3.11E−05 | 5.84E−05 | 2 | No Gel |
| 3 | HMW | 1.51E−05 | 1.72E−05 | 1 | No Gel |
| 4 | LMW | 2.47E−05 | 3.20E−04 | 13 | Gel |

Example 4

Dynamic Mechanical Thermal Analysis (DMTA) of PVA/HDA and PVA/TIP

Films from Examples 1-3 above were stored in a desiccator until ready for the DMTA study, to prevent moisture uptake.

The films were then cut into thin strips (on the order of 3-5 mm width×20 mm length×40 mm thick) and DMTA performed as a temperature sweep from −100° C. to 400° C. at a rate of 10° C./minute on the resultant specimens. Although the films should have been completely dry, it is expected that they contained some residual DMSO, the solvent used in the synthesis.

Figure 1:
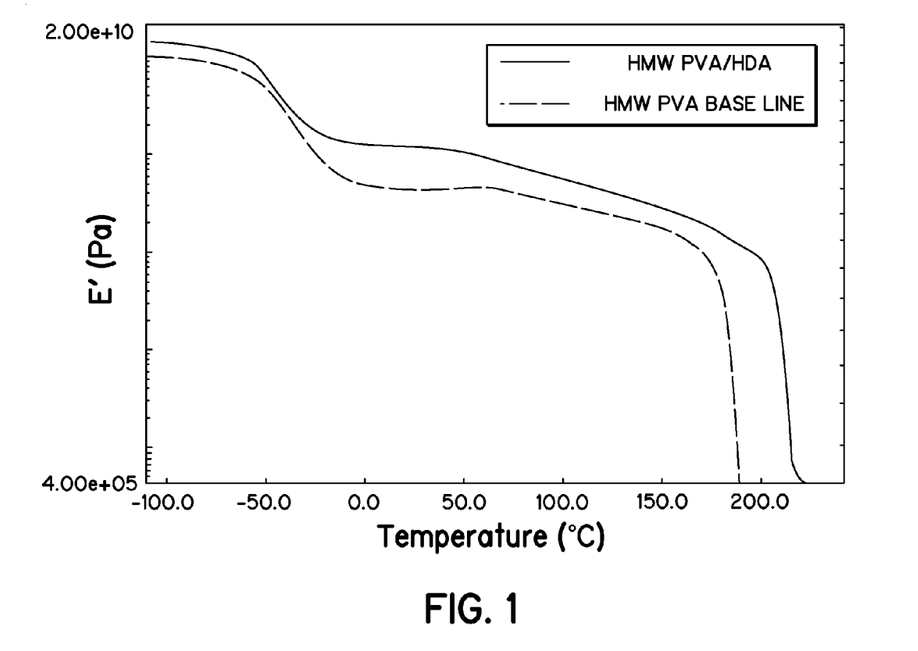
FIG. 1 shows Dynamic Mechanical Thermal Analysis (DMTA) of high molecular weight polyvinyl alcohol (HMW PVA) versus HMW PVA/4,4'-(hexafluoroisopropylidene) diphthalic anhydride (HDA) according to one embodiment of the invention.
Figure 2:
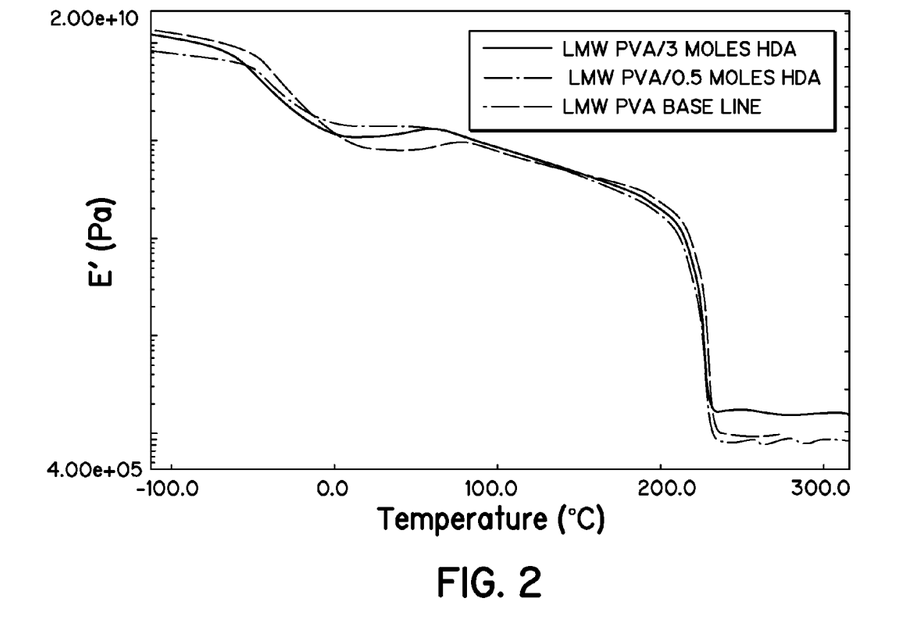
FIG. 2 shows DMTA of low molecular weight polyvinyl alcohol (LMW PVA) versus LMW PVA/HDA (0.25 and 3 moles HDA) according to one embodiment of the invention.

The DMTA traces for the HMW PVA baseline and 1 mole HMW PVA to 0.5 moles HDA are shown in FIG. 1. From the traces, it is evident that the PVA/HDA shows a significant increase in storage modulus (~6×10$^8$ Pa increase at 98° F. (37° C.)). The increase in storage modulus for the PVA/HDA was more than double that of the baseline PVA. In addition, the melting point increased approximately 25° C. The DMTA traces for the LMW PVA/HDA films along with the LMW PVA baseline in FIG. 2 show an increase in storage modulus with no increase in melting temperature.

Figure 3:
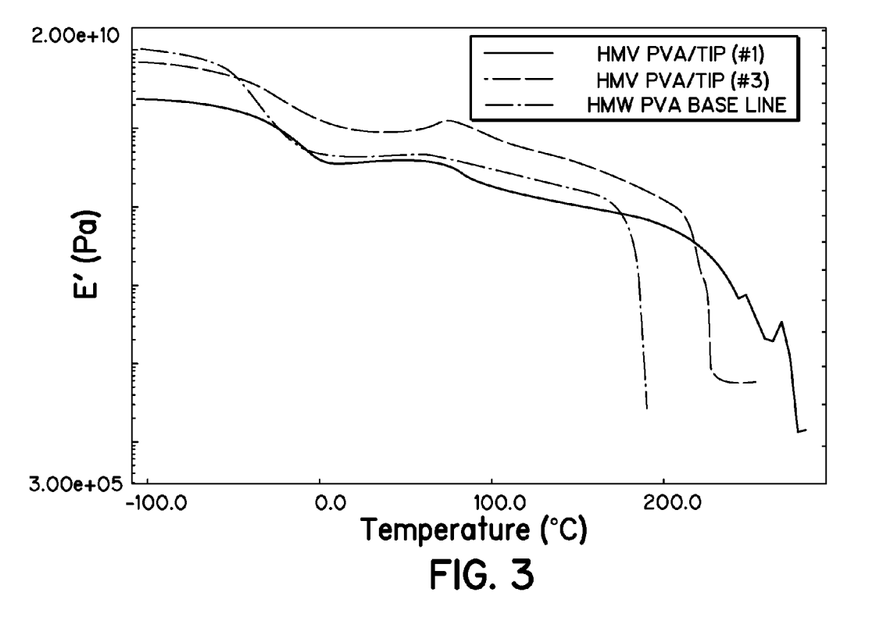
FIG. 3 shows DMTA of HMW PVA versus HMW PVA/titanium (IV) isopropoxide (referred to as TIP), at either a mole ratio of 20:1(#1) or 1:1(#3) TIP:PVA, according to other embodiments of the invention.
Figure 4:
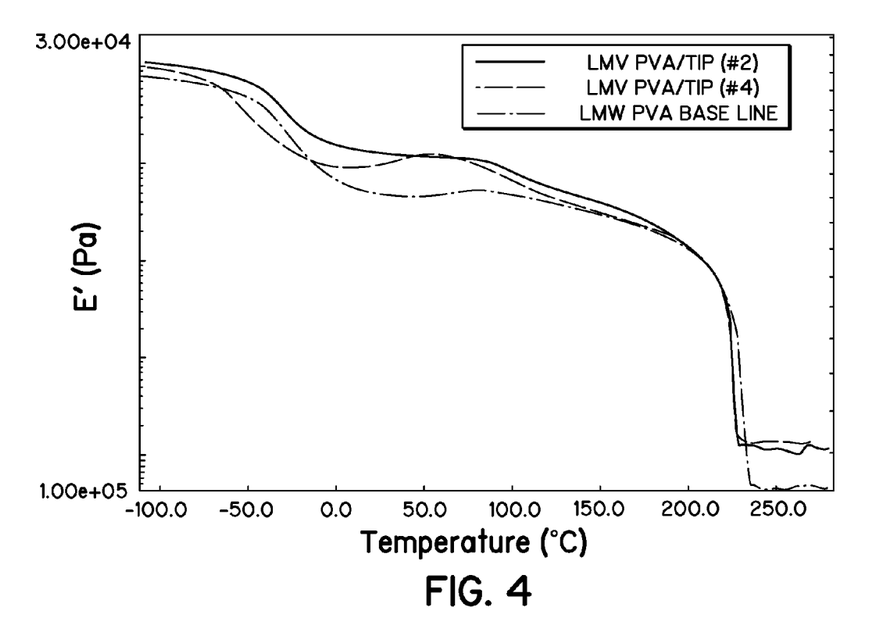
FIG. 4 shows DMTA of LMW PVA versus LMW PVA/TIP, at either a mole ratio of 2:1(#2) or 13:1(#4) TIP:PVA, according to other embodiments of the invention.

The DMTA traces for the PVA/TIP films are shown in FIG. 3 and FIG. 4 using the HMW PVA and LMW PVA, respectively. For both LMW PVA and HMW PVA, the storage modulus shows more than a two-fold increase for the lower mole ratio PVA/TIP films (reactions 2 and 3, Table 1), or approximately 6×10$^8$ Pa increase in the storage modulus at 37° C.

In summary, all of the synthetic approaches to improve the storage modulus of the baseline PVAs through chain modification were successful. This work showed that PVA can be modified using 4,4'-(hexafluoroisopropylidene) diphthalic anhydride (HDA) or titanium (IV) isopropoxide (TIP) to increase mechanical properties, specifically storage modulus.

Example 5

Synthesis of PVA/PEI Hydrogel

ULTEM® is a polyetherimide (PEI) that is an amorphous polymer possessing high strength and heat resistance. Experiments were conducted evaluating a PVA/ULTEM® phase separated, branched, copolymer hydrogel. First, a solvent study was performed to determine the best solvent to use for dissolving ULTEM® and PVA. This was accomplished by adding approximately 1 wt. % to varying solvents and then heating the solutions. From this study, two solvents were found that would dissolve both ULTEM® and PVA, dimethyl formamide (DMF) and DMSO. However, the ULTEM® appeared to come back out of solution upon cooling when greater than 1 wt. % solutions were attempted. Next, an investigation using a combination of two different solvents for ULTEM® and PVA was conducted using methyl chloride (MeCl)/DMSO, DMF/DMSO and just DMSO with the PVA and ULTEM®. From this study, DMSO was the best solvent because DMSO has preferred biocompatibility properties and ultimately dissolved the materials as well as the other solvents tested.

ULTEM® and PVA, both using DMSO as the solvent, were mixed at a ratio of 10% ULTEM® to 90% PVA. 5-7 wt. % solutions were made from the HMW PVA, while 10-20 wt. % solutions were made from the LMW PVA. The solutions were mixed to form the 10% ULTEM®/90% PVA mixtures along with various amounts of diethyl carbonate (DEC) (a crosslinking agent) and sulfuric acid (a reaction initiator) (see Table 2). The solutions were then cast into films, dried at 70° C. for 24 hours, and placed in a desiccator for storage.

TABLE 2

Various solutions made from the 10%/90% ULTEM ®/PVA mixtures

| PVA | ULTEM ® | DEC | SULFURIC ACID |
| --- | --- | --- | --- |
| HMW | 1 mole | 2 mole | 1 drop |
| HMW | 1 mole | 2 mole | 2 drops |
| HMW | 1 mole | 10 drops | 1 drop |
| LMW | 1 mole | 2 mole | 1 drop |
| LMW | 1 mole | 2 mole | 2 drops |
| LMW | 1 mole | 5 drops | 2 drops |

Figure 5:
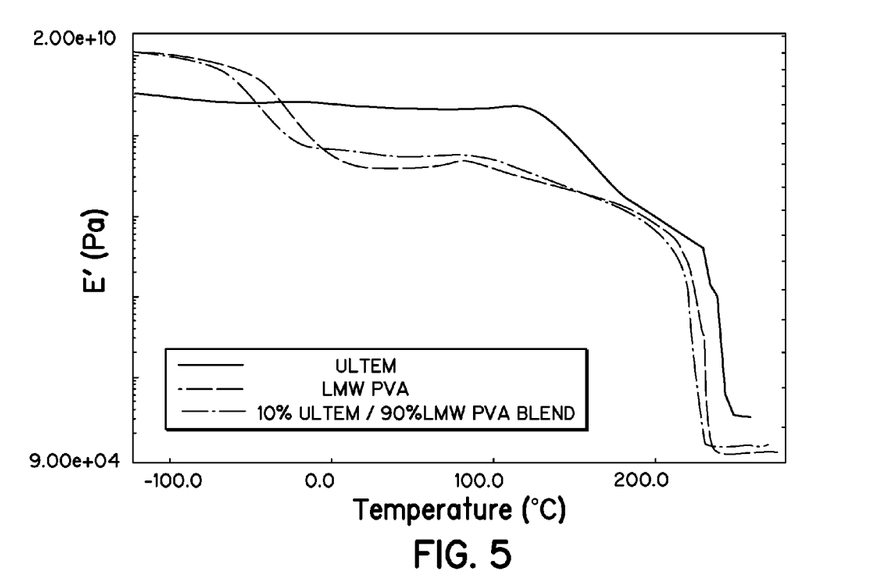
FIG. 5 shows DMTA of LMW PVA and ULTEM® versus LMW PVA/ULTEM® blend according to one embodiment of the invention.
Figure 6:
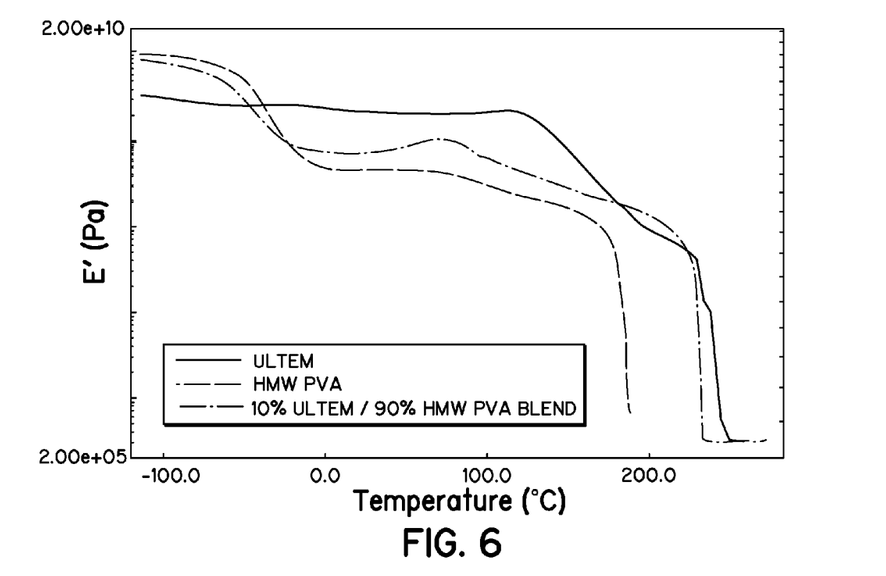
FIG. 6 shows DMTA of HMW PVA and ULTEM® versus HMW PVA/ULTEM® blend according to one embodiment of the invention.

The DMTA traces for the baseline films and the 10% ULTEM® and 90% LMW PVA blend are shown in FIG. 5. The PVA/PEI showed an increase in storage modulus of about 2×10$^8$ Pa (29,000 psi) over the baseline LMW PVA and no increase in melt temperature. The HMW PVA/ULTEM® blend showed an increase in storage modulus of about 3×10$^8$ Pa (41,500 psi) over the baseline HMW PVA (FIG. 6) and an increase in melt temperature.

Figure 7:
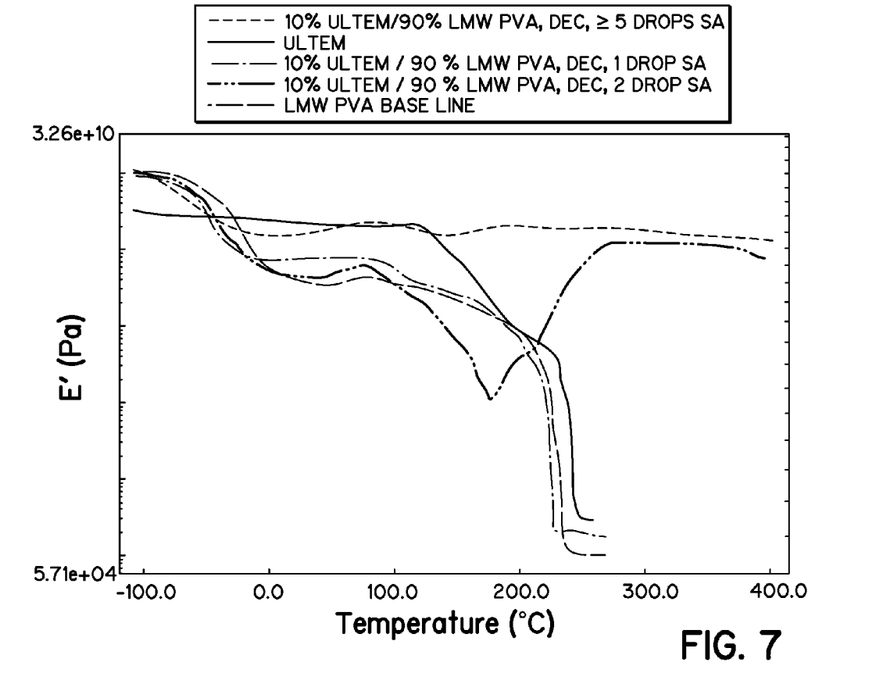
FIG. 7 shows DMTA of LMW PVA and ULTEM® versus LMW PVA/ULTEM®/diethyl carbonate (DEC) blends, with 1 or 2 drops of sulfuric acid (SA), according to other embodiments of the invention.
Figure 8:
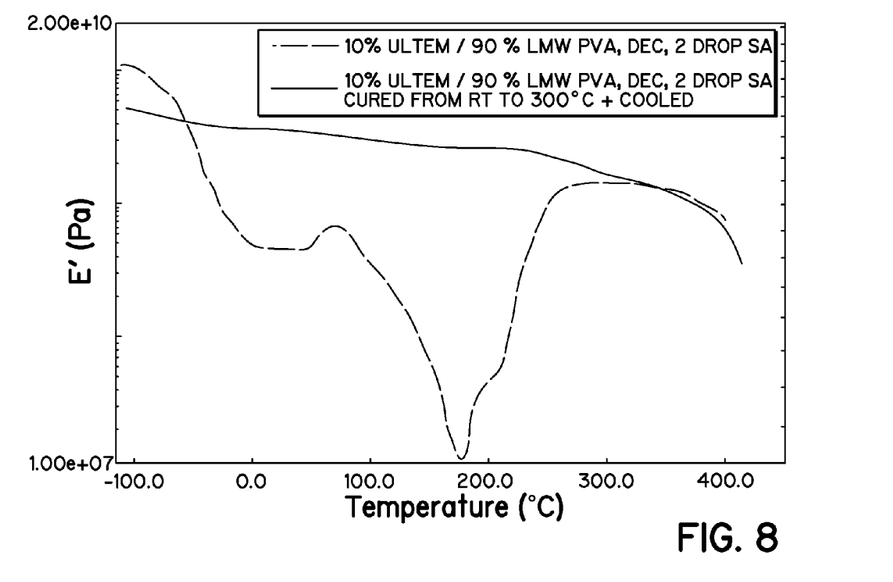
FIG. 8 shows DMTA of LMW PVA/ULTEM®/diethyl carbonate (DEC)/2 drops SA subjected to either the standard curing process or an alternative curing process according to another embodiment of the invention.

The DMTA traces for the LMW PVA/ULTEM® synthesized films using DEC and sulfuric acid are shown in FIG. 7. All of the synthesized films show an improvement in storage modulus at 98° F. (36.6° C.) except the film made using 2 moles of DEC to 1 mole of ULTEM® with 2 drops of sulfuric acid. However, the DMTA trace of this film shows that the storage modulus increases after its initial drop, indicating that this specimen was curing during the DMTA run. Therefore, this specimen was subjected to an alternate curing temperature (FIG. 8). In this alternate procedure, the specimen was subjected to a temperature change from RT to 300° C. to cure the specimen, and then cooled. The film resulting from the alternate procedure showed a storage modulus at 98° F. of approximately 3.5×10$^9$ Pa, or a 3.1×10$^9$ Pa increase in storage modulus over the baseline LMW PVA and a 1.5×10$^9$ Pa increase over the baseline ULTEM® (FIG. 7), and the melting point was increased to 400° C. This increase in storage modulus and melting point was similar for the 5 drops DEC to 2 drops sulfuric acid ULTEM®/PVA film without the need to cure any further. Therefore, it appears that there is a critical ratio of sulfuric acid to DEC needed to initiate the reaction. In any case, all of the films showed marked improvement over the baseline LMW PVA film. Referring again to FIG. 7, one sample was tested with an excess of sulfuric acid (≧5 drops). The sample turned black, indicating that it was driven to a completely reacted state by the sulfuric acid. The sample exhibited little change in the storage modulus with increasing temperature, and had a rubbery nature, and thus will not degrade with increasing temperature, thereby providing stability and durability.

Figure 9:
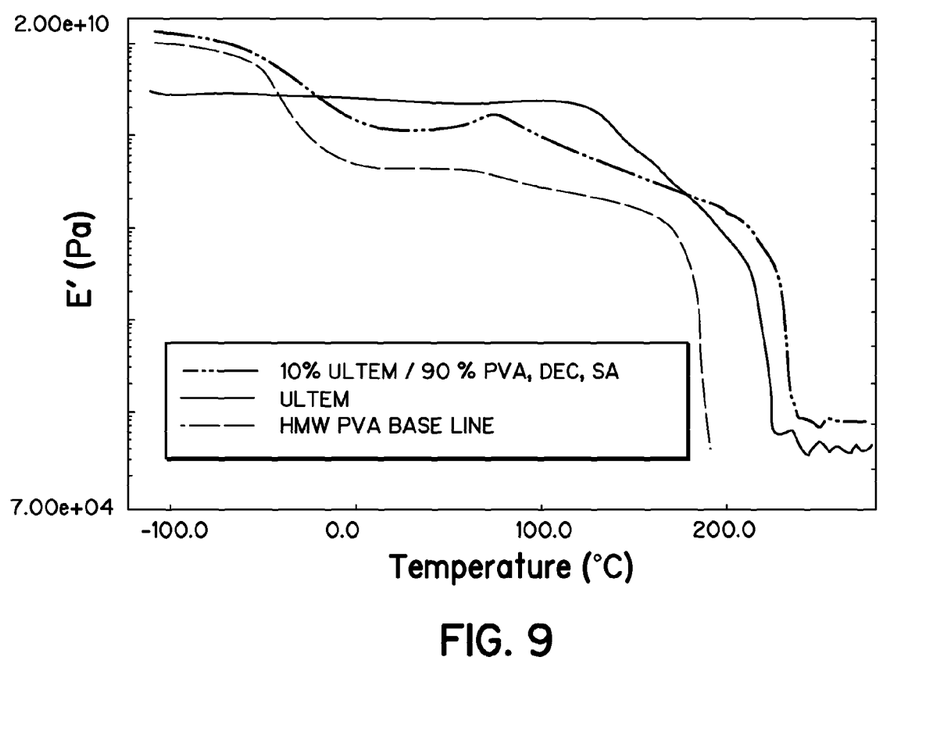
FIG. 9 shows DMTA of HMW PVA and ULTEM® versus HMW PVA/ULTEM®/diethyl carbonate (DEC)/2 drops SA according to another embodiment of the invention.

The DMTA traces for the HMW PVA/ULTEM® synthesized films using DEC and sulfuric acid are given in FIG. 9. All of these films showed marked improvement in storage modulus (increase of 6×10$^8$ Pa) over the baseline HMW PVA, without the need for additional curing, except for the 10% ULTEM®/90% HMW PVA/10 drops DEC/1 drop sulfuric acid film. In addition, all of the ULTEM®/PVA films showed a melting point near or above that of the ULTEM® alone. We attempted to re-run the 10% Ultem™/90% HMW PVA/10 drops DEC/i drop sulfuric acid film from RT to 200-300° C., but the film melted to much to re-run. However, when this film was run to higher temperature, it was obvious that further curing was occurring. This infers that either more heat or more catalyst is needed for this particular material to fully cure.

In summary, all of the synthetic and blended materials using 10% ULTEM® showed marked improvement over the baseline LMW PVA and HMW PVA films. In addition, the ULTEM®-containing materials have a melting point that indicates that they can be melt processed above the melting point.

Example 6

Determination of Equilibrium Water Absorption Amount

Samples from the films created above were cut into specimens approximately 2 inches long by ¼ inch wide. The samples were placed in a desiccator to assure that the specimens gained no moisture prior to the saturation study. The specimens were then put in beakers containing de-ionized water at 98° F. (36.6° C.) and their weight monitored as a function of time. The saturation values are given in Table 3 and were taken after the samples' weight reached an asymptotic value (49.4 hours) and Table 4 gives the sampling time.

TABLE 3

Hydrogel Saturation Weight Gain after 49.4 hours

| SAMPLE | SAMPLE ID | WEIGHT GAIN (%) | MATERIAL NOTES |
|---|---|---|---|
| ZS-1 | HP-1 | 130 | HMW PVA Baseline |
| ZS-T | HP-2 | 128 | HMW PVA Baseline (control) |
| ZS-2 | LP-1 | 115 | LMW PVA Baseline |
| ZS-3 | UD | 1 | ULTEM ® Baseline |
| ZS-4 | HP-TIP#1 | 92 | HMW PVA/TIP #1 film |
| ZS-5 | LP-TIP#4 | 148 | LMW PVA/TIP #4 film |
| ZS-6 | LP-HDA | 119 | LMW PVA/HDA Rx2 - Branched |
| ZS-7 | HP-HDA | 85 | HMW PVA/HDA Rx3 - Branched |
| ZS-8 | LP-10U-5DEC-2SA | 25 | 90% LMW PVA/10% ULTEM ®/5 drops DEC/2 drops SA |
| ZS-10 | LP-10U-2DEC-2SA | 1617 | 90% LMW PVA/10% ULTEM ®/2 moles DEC/2 drops SA |
| ZS-9 | LP-10U-2DEC-2SA-HT | 3 | 90% LMW PVA/10% ULTEM ®/2 moles DEC/2 drops SA - heat treated to 300° C. |
| ZS-12 | HP-10U-2DEC-2SA | 82 | 90% HMW PVA/10% ULTEM ®/2 moles DEC/2 drops SA |
| ZS-11 | HP-10U-2DEC-2SA-HT | 36 | 90% HMW PVA/10% ULTEM ®/2 moles DEC/2 drops SA - heat treated to 200° C. |
| ZS-13 | HP-10U | 85 | 90% LMW PVA/10% ULTEM ® |
| ZS-14 | LP-10U | 47 | 90% HMW PVA/10% ULTEM ® |

TABLE 4

Sampling Time

| SAMPLE | TIME (MIN) |
|---|---|
| 1 | 45 |
| 2 | 88 |
| 3 | 160 |
| 4 | 2920 |
| 5 | 2965 |

The samples were then run in the DMTA from RT to 55° C. and held for 5 minutes. A summary of the results is given in Table 5. Areas in the table that are blank are instances where the film broke and could not be run. The table also gives the percent increase in storage modulus. All percent increase calculations were based on the HMW PVA baseline.

TABLE 5

Storage Modulus taken at ~37° C. for Saturated Hydrogels

| SAMPLE | SAMPLE ID | E' (Pa) @ 37° C. | % INCREASE |
|---|---|---|---|
| ZS-1 | HP-1 | 2.99E+05 | |
| ZS-T | LP-1 | | |
| ZS-2 | UD | 1.54E+09 | |
| ZS-3 | HP-TIP#1 | 9.46E+06 | 3068% |
| ZS-4 | LP-TIP#4 | 1.21E+08 | 40489% |
| ZS-5 | LP-HDA | | |
| ZS-6 | HP-HDA | 3.12E+06 | 944% |
| ZS-7 | 90LP-10U-5DEC-2SA | 6.00E+08 | 200838% |
| ZS-8 | 90LP-10U-2DEC-2SA-HT | | |
| ZS-10 | 90LP-10U-2DEC-2SA | | |
| ZS-9 | 90HP-10U-2DEC-2SA-HT | 4.23E+08 | 141662% |
| ZS-12 | 90HP-10U-2DEC-2SA | 3.21E+07 | 10637% |
| ZS-11 | 90HP-10U | 3.73E+07 | 12378% |
| ZS-13 | 90LP-10U | | |
| ZS-14 | HP-2 | | |

In summary, the phase separated, branched, copolymer hydrogels produced gave a wide range of water saturation values ranging from 3 percent to 1617 percent weight increase. The increase in water saturation values demonstrates the ability to control water absorption using molecular structure. All of the inventive hydrogels showed improvement in storage modulus at 98° F. that ranged from about 900 to about 200,000 percent increase. Overall, incorporation of ladder polymers (i.e., a polymer in which two main polymer chains or backbones are bonded together at regular intervals), specifically ULTEM®, into PVA and increasing the molecular weight through branching or cross-linking, resulted in significant increases in the mechanical properties of the PVA materials.

What is claimed is:

1. An implantable medical device comprising:
   a composition comprising a phase separated, branched, hydrogel, the hydrogel formed by polymerizing a hydrophilic polymer and a polymer chain modifying agent in the presence of a crosslinking agent and a reaction initiator such that the hydrophilic polymer and polymer chain modifying agent are chemically bonded to one another; and
   wherein the phase separated, branched, copolymer hydrogel has a greater mechanical strength and a higher melting temperature than the hydrophilic polymer; and
   wherein the polymer chain modifying agent is a polyetherimide.

2. The device of claim 1 wherein the hydrophilic polymer is a polyhydroxy-containing polymer.

3. The device of claim 1 wherein the hydrophilic polymer is a polyvinyl alcohol, a polyacrylamide, or combinations thereof.

4. An implantable medical device comprising a phase separated, branched, hydrogel comprising a hydrophilic polymer and a polymer chain modifying agent chemically bonded to one another, wherein the polymer chain modifying agent is a polyetherimide; and
   wherein the phase separated, branched, copolymer hydrogel has a greater mechanical strength and a higher melting temperature than the hydrophilic polymer.

5. The device of claim 4 wherein the hydrophilic polymer is a polyhydroxy-containing polymer.

6. The device of claim 4 wherein the hydrophilic polymer is a polyvinyl alcohol, a polyacrylamide, or combinations thereof.

7. The device of claim 4 wherein the device is used in nucleoplasty or medial compartment tibial resurfacing.

* * * * *